United States Patent
Kendall et al.

(10) Patent No.: US 7,229,646 B2
(45) Date of Patent: Jun. 12, 2007

(54) METHODS AND COMPOSITIONS FOR MODULATING IMMUNE RESPONSE AND FOR THE TREATMENT OF INFLAMMATORY DISEASE

(75) Inventors: Roger V. Kendall, West Haven, CT (US); John Lawson, Clemson, SC (US)

(73) Assignee: Foodscience Corporation, Essex Junction, VT (US)

( * ) Notice: Subject to any disclaimer, the term of this patent is extended or adjusted under 35 U.S.C. 154(b) by 510 days.

(21) Appl. No.: 10/391,645

(22) Filed: Mar. 20, 2003

(65) Prior Publication Data

US 2003/0180288 A1 Sep. 25, 2003

Related U.S. Application Data

(62) Division of application No. 09/316,001, filed on May 21, 1999, now abandoned.

(51) Int. Cl.
*A61K 35/36* (2006.01)
(52) U.S. Cl. .................. 424/547; 424/278.1
(58) Field of Classification Search .............. None
See application file for complete search history.

(56) References Cited

U.S. PATENT DOCUMENTS

| | | |
|---|---|---|
| 4,385,068 A | 5/1983 | Kendall et al. |
| 4,801,453 A | 1/1989 | Kosuge et al. |
| 4,994,492 A | 2/1991 | Kendall et al. |
| 5,026,728 A * | 6/1991 | Kendall et al. ............ 514/561 |
| 5,118,618 A | 6/1992 | Kendall et al. |

FOREIGN PATENT DOCUMENTS

| | | |
|---|---|---|
| WO | WO 96 05164 | 2/1996 |
| WO | WO 9605164 A1 * | 2/1996 |
| WO | WO 98 48816 | 11/1998 |

OTHER PUBLICATIONS

Bewkowski, Stanley, 1991, The humoral response to collagen and the effects of dimethylglycine and *Perna canaliculus* on collagen induced arthritis in rats. Thesis Dissertation.*
Petri, Michelle, 1998, Treatment of systemic lupus erythematosis: an update. American Family Physician, vol. 57 p. 1-11.*
Gibson et al., 1980, *Perna canaliculus* in the treatment of arthritis, Clinical Trials. vol. 224: 955-860.*

(Continued)

*Primary Examiner*—G. R. Ewoldt
*Assistant Examiner*—Amy Juedes
(74) *Attorney, Agent, or Firm*—Millen, White, Zelano & Branigan, P.C.

(57) ABSTRACT

Compositions and methods for treating inflammatory disease and for modulating the immune system are described. The compositions and methods pertain to the use of a combination of N,N-dimethylglycine and a component derived from the mussel *Perna canaliculus* to achieve synergistic anti-inflammatory and immunomodulating effects.

9 Claims, 7 Drawing Sheets

OTHER PUBLICATIONS

Whitehouse et al., 1997, Anti-inflammatory activity of a lipid fraction (lyprinol) from the NZ green lipped mussel. Infammopharmacology, vol. 5: 237-246.*

Levine et al., "Effect of a Nutritional Supplement containing N,N-Dimethylglycine (DMG) on the Racing Standardbred," Equine Practice, vol. 4, No. 3, Mar. 1982.

Reap et al., "Stimulation of the immune response by dimethylglycine, a nontoxic metabolite," The J. of Laboratory and Clinical medicine, vol. 115, No. 4, Apr. 1990, pp. 481-486.

Audeval et al., Reprint from Gazette Medicale, vol. 93, No. 38, 1986, *Therapeutic News*, Controlled doubled-blind study against a placebo of the mussel extract *Perna canaliculus* (green-lipped mussel) in arthritis of the knee.

Eng. M. Tan, "Antinuclear Antibodies: Diagnostic Markers for Autoimmune Diseases and Probes for Cell Biology," Advances in Immunology, vol. 44, pp. 93-151.

Whitehouse et al., "Anti-Inflammatory Activity of a Lipid Fraction (Lyprinol) from the NZ Green-Lipped Mussel," Inflammopharmacology, vol. 5, pp. 237-247 (1997).

Gibson et al., "*Perna canaliculus* in the treatment of arthritis," Clinical Trials, vol. 224, pp. 955-960 (1980).

Graber et al., "Immunomodulating Properties of Dimethylglycine in Humans," J. of Infectious Diseases, vol. 143, No. 1 Jan. 1981, pp. 101-105.

* cited by examiner

METHODS AND COMPOSITIONS FOR MODULATING IMMUNE RESPONSE AND FOR THE TREATMENT OF INFLAMMATORY DISEASE

This application is divisional of U.S. Ser. No. 09/316,001, filed May 21, 1999 now abandoned.

BACKGROUND OF INVENTION

This invention relates to the use of N,N-dimethylglycine (DMG) in combination with at least one component derived from *Perna canaliculus* to modulate immune responses and to treat inflammatory diseases in man or animals.

N'N-dimethylglycine (DMG), which is a tertiary amino acid, is an intermediary metabolite found in low levels in many foods. It is produced in the body from choline and has been used as a non-fuel nutrient. The physiological and potential therapeutic effects of N,N-dimethylglycine have been evaluated in recent years. References in the literature pertaining to N,N-dimethylglycine and its potential uses include the following: Graber et al., 1981, *J. of Infectious Diseases* 143:101–105 (DMG stimulation of both humoral and cellular immunity); Kendall and Graber, U.S. Pat. No. 4,385,068 (discusses DMG alleviation of the effects of excess radiation on the immune system); the 1980 Pacific Slope Biochemical Conference, a paper entitled "Decrease of Lactic Acid Concentration in Blood of Animals Given N,N-Dimethylglycine"; March, 1982 issue of *Equine Practice*, an article entitled "Effect of a Nutritional Supplement Containing N,N-Dimethylglycine (DMG) on the Racing Standardbred" (DMG increased oxygen utilization and thereby decreased lactic acid levels in animals under extreme stress); November-December, 1982 issue of *Canine Practice*, an article entitled "A Clinical Evaluation of N,N-Dimethylglycine (DMG) and Diisopropylammonium Dichloroacetate (DIPA) on the Performance of Racing Greyhounds"; February, 1987 issue of *Let's Live* magazine, an article entitled "Dimethylglycine Update, New Studies Confirm DMG Improves Health" (DMG as an immunomodulating agent); February, 1987 issue of *Health Consciousness*, an article entitled "N,N-Dimethylglycine and the Immune Response" (DMG as an immunomodulating agent); 1987 ASM Annual Meeting, a paper entitled "The Effect of DMG on the Immune Response of Rabbits" (DMG as an immunomodulating agent); Jun. 27, 1987 issue of *The Blood Horse*, an article entitled "DMG, Properties and Proprieties" (in humans, DMG stimulated B-cells to produce much higher antibody responses, and DMG enhanced the activity of T cells and macrophages); Kendall et al., U.S. Pat. No. 4,994,492 (treatment of melanoma using DMG); Kendall and Lawson, U.S. Pat. No. 5,026,728 (treatment of arthritis and inflammation using DMG); Kendall and Lawson, U.S. Pat. No. 5,118,618 (use of DMG to enhance antibody production).

The use of preparations made from *Perna canaliculus* for therapeutic effect extends back at least twenty-five years since the mid-seventies. The nutritional and therapeutic properties of freeze-dried *Perna canaliculus* in alleviating the symptoms of arthritis were reported in Croft, 1979, *Relief From Arthritis* (Thorsons Publishing Group, Rochester, Vt.). Studies in both animal and human experiments have given mixed results, but indicate overall that certain components in the mussels were potentially helpful in relieving inflammation and pain associated with arthritis. Certain of these studies are as follows: McFarlane, June 1975, *New Zealand Medical Journal*, pg. 569 (the results of a study of the effects of a *Perna canaliculus* product called "Seatone" on a small group of arthritic individuals were reported); Rainsford and Whitehouse, 1980, *Arzeim-Forsch*, pg. 2128–2131 (a freeze-dried powdered preparation of whole mussel which ws given orally to rats showed some modest anti-inflammatory activity in an induced rheumatoid arthritis model); Miller and Ormrod, 1980, *The New Zealand Medical Journal* 92:187 (a crude fraction of *Perna canaliculus* had a marked anti-inflammatory effect when administered by intra peritoneal injection in rats); Couch et al., 1982, *The New Zealand Medical Journal* 95:803 (a protein containing fraction of *Perna canaliculus* had an anti-inflammatory effect); Caughey et al., 1983, *European Journal of Rheumatology and Inflammation* 6:197 (in a human study involving forty-seven rheumatoid arthritic patients, no improvement was observed in patients given mussel extract as compared to patients taking the anti-inflammatory drug naproxen); Gibson et al., 1980, *Practitioner* 224:955 (93: 111 (in human trials for both osteoarthritis and rheumatoid arthritis, significant benefits were achieved after three months on a *Perna canaliculus* preparation, including reduced pain and stiffness and improvement on functional tests); Audeval and Bouchart, 1986, *Gazette Medicale* 93:111 (in human trials for osteoarthritis, forty percent of subjects showed significant improvement after treatment with a *Perna canaliculus* preparation); Miller et al., 1993, *Agents Actions* 38:139 (an aqueous fraction of *Perna canaliculus* inhibited experimentally induced inflammation in rats); Whitehouse et al., 1997, *Inflammopharmacology* (a lipid extract of *Perna canaliculus* exhibited a dose related anti-inflammatory activity).

SUMMARY OF THE INVENTION

In accordance with this invention, it has been discovered that a combination of N,N-dimethylglycine (DMG) and a component derived from *Perna canaliculus* (referred to herein as *Perna canaliculus* extract (PCE)) has a synergistic effect in the treatment of inflammatory disease. In particular, it has been discovered that the combination has a synergistic effect in the treatment of autoimmune disease, including lupus erythmatosus, and in the modulation of immune responses to inflammatory disease. Also in accordance with this invention it has been discovered that the aberrant immune response profiles in humans with rheumatoid arthritis or osteoarthritis may be beneficially altered by the administration of a combination of DMG and PCE.

Treatment, as used herein, pertains to the therapeutic administration of the compounds of the invention for the prevention, amelioration, or cure of disease.

Inflammatory diseases that may be treated in accordance with this invention include systemic autoimmune diseases such as, for example, lupus erythmatosus, rheumatoid arthritis, and multiple sclerosis, and organ specific autoimmune diseases such as, for example, myasthenia gravis, Grave's disease, Hashimoto's thyroiditis, Crohn's disease, autoimmune hemolytic anemias, insulin dependent diabetes mellitus, glomerulonephritis, and rheumatic fever. Other inflammatory diseases that may be treated in accordance with this invention include other inflammatory arthritic conditions such as osteoarthritis and gouty arthritis, as well as other inflammatory conditions such as conjunctivitis, dermatitis, bronchitis, rhinitis etc., brought about by injury, allergies, infections, microorganisms, trauma, or physical or chemical agents. Additionally, the treatment of inflammatory aspects of asthma is also contemplated as part of this invention.

One aspect of the invention is a composition comprising a combination of a DMG component and at least one PCE component. The PCE component may be any therapeutically active component derived from the flesh of the mussel or its organs, which are suitable for use in the preparation of food supplements or pharmaceutical preparations. The invention contemplates the use of unrefined components of the mussel, such as whole mussel, or any therapeutically active extracts thereof. As used herein, a therapeutically active PCE component according to this invention is a component that is effective in reducing inflammation in animals or humans or that has immunomodulating effects in humans or animals. For example, several animal models for arthritis that are well known in the art may be used to determine therapeutic activity of a PCE component. Such models include, for example, collagen induced arthritis in rats or mice, carrageenan-induced inflammatory oedema in rats as described in Miller et al., 1980, *New Zealand Medical Journal* 92:667, and arthritis induced in rats and mice by the injection of adjuvants prepared from dried *Mycobacterium tuberculosis* as described in Whitehouse, et al., 1997, *Inflammopharmacology* 5:237–246. Therapeutic activity of a PCE component may also be determined by evaluating whether the PCE component is effective for reducing anti-nuclear antibodies, particularly anti-ssDNA antibodies or anti-dsDNA antibodies, in humans with SLE or in the mouse model for SLE, as described in the examples. In particular, the PCE may be a preparation of whole mussel which has been freeze-dried and ground such as, for example, the Sea Mussel product available from FoodScience Corporation, Essex Junction, Vt. or the *Perna* product available from DaVinci Laboratories, Essex Junction, Vt. Additionally, therapeutically active extracts of *Perna canaliculus* may also be employed. Such therapeutically active extracts have been described as follows: Macrides and Kalafatis, PCT/AU95/00485, WO 96/05164 (a purified lipid extract); Whitehouse et al., 1997, *Inflammopharmacology* 5:237–246 (a purified lipid extract); Kosuge and Sugiyama, U.S. Pat. No. 4,801,453 (stabilized mussel extract); Couch et al., 1982, *The New Zealand Medical Journal* 95:803 (a protein fraction); Miller et al., 1993, *Agents Actions* 38:139 (an aqueous fraction).

The DMG component may be N,N-dimethylglycine or a pharmacologically acceptable salt thereof. A composition containing both DMG and PCE may be formulated as a pharmaceutical or dietary supplement using techniques that are well known in the art. A preferred formulation of the composition is a formulation for oral administration.

Another aspect of this invention is a method of treating inflammatory disease comprising administering to an animal a combination of both a DMG component and at least one PCE component. As used herein, the term animal includes, but is not limited to, mammals. Preferred mammals include humans, horses, farm animals and household pets. The DMG and PCE components may be administered via the same route or they may be administered via different routes. For example, the DMG and PCE may both be administered orally, either simultaneously or at different times. A preferred route for administration of PCE, particularly ground whole mussel, is via oral administration. A preferred route for the administration of DMG is via oral administration, particularly as an admixture with water. DMG or PCE can also be administered by intramuscular injection, intra peritoneal injection, parenteral administration, etc.

The DMG and PCE used in this invention can be employed in admixture with conventional excipients, i.e. pharmaceutically acceptable organic or inorganic carrier substances suitable for parenteral, enteral (e.g., oral) application which do not deleteriously affect the active compound. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium sterate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and, if desired, mixed with auxiliary agents such as, for example, lubricants, preservatives, stabilizers, wetting agents, emulsifiers, salts for influencing osmotic pressure, buffers, coloring agents, flavoring agents and/or aromatic substances and the like which do not deleteriously affect the active compound. Other pharmaceutically acceptable carriers include aqueous solutions, non toxic excipients, including salts, preservatives, buffers and the like, as described for instance, in *Remington's Pharmaceutical Sciences*, 18th ed. (1990), Mack Publishing Co., Easton, Pa., the contents of which are hereby incorporated by reference. The pH and exact concentration of the various components of the pharmaceutical composition are adjusted according to routine skills in the art. See Gilman et al. (eds.) (1990) *Goodman and Gilman's: The Pharmacological Bases of Therapeutics*, 8th ed., Pergamon Press. The DMG and/or PCE can also be combined where desired with other active agents, including PCE or DMG respectively.

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the patient, different daily doses are necessary. Under certain circumstances, however, higher or lower daily doses may be appropriate. The average daily dosage of the compounds of this invention, when used to treat inflammatory disease or to modulate the immune response are typically the following: for DMG, the average daily dose is generally about 1 to about 500 mg/kg/day, preferably about 10 to about 100 mg/kg/day, more preferably about 2 to about 30 mg/kg/day; for PCE, when the PCE comprises ground whole mussel, the average daily dose is generally about 1 to about 500 mg/kg/day, preferably about 10 to about 100 mg/kg/day, more preferably about 20 to about 60 mg/kg/day. For PCE components other than ground whole mussel, the average daily dose may vary but can be readily determined by one of skill in the art. The daily dosage may be administered as a single dose per day or as a plurality of divided doses per day. The daily dosage may also be administered on a non-daily basis, such as for example, every second or third day, provided an average daily dose as described above is achieved.

The combination PCE and DMG can be administered concurrently or alternately with other therapeutic treatments conventionally employed to treat inflammatory disease. For example, for the treatment of lupus erythmatosus, rheumatoid arthritis, and osteoarthritis, PCE and DMG may be administered in conjunction anti-inflammatory agents, including both coticosteroid agents such as, for example, prednisone or methylprednisolone and non-steroidal anti-inflammatory agents such as, for example, salicylates and ibuprofen. For the treatment of lupus erythmatosus, for example, the compounds of this invention may also be administered in conjunction with anti-malarial drugs including, for example, hydroxychloroquinone or in conjunction with cytotoxic chemotherapies including, for example, azathioprine and cyclophosphamide.

Another aspect of this invention is a method of treating systemic lupus erythmatosus comprising administering a combination of DMG and PCE. In a preferred embodiment, the administration of the combination reduces the serum concentration of anti-nuclear antibodies such as, for example, anti-nuclear antibodies that bind to chromatin, nucleosomes, histone/DNA complexes, histones, double-stranded DNA (dsDNA), single-stranded DNA (ssDNA), double-stranded RNA (dsRNA), single-stranded RNA (ss-RNA), and transfer-RNA (tRNA). Preferably, the serum concentration of anti-ssDNA and/or anti-dsDNA antibodies are reduced.

Another aspect of this invention is a method modulating the immune response in an animal, particularly an animal with an autoimmune disease or other inflammatory disease by the administration of a combination of DMG and PCE, wherein any of the following effects on the immune response, or any combination thereof, are achieved: a decrease in the serum levels of interleukin 6 (il-6), a decrease in the serum levels of interleukin 10 (il-10), an increase in the serum levels of tumor necrosis factor-α (TNF-α), or a decrease in the concentration of $CD8^+$ lymphocytes in the blood. These effects typically counteract aberrant immune profiles observed in inflammatory disease. A preferred effect is a decrease in the serum levels of il-10 or a decrease in CD8+ lymphocytes in the blood.

Another aspect of this invention is a kit containing a combination of DMG and PCE formulations. Particularly preferred is kit containing both DMG and PCE formulations that are useful for oral administration, preferably as dietary supplements. A kit would typically provide for an average daily dose of PCE or DMG as described above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure.

EXAMPLES

In the following examples, all parts and percentages are by weight unless otherwise indicated.

Example 1

Preparation of a Therapeutically Active PCE Component

A therapeutically active formulation of *Perna canaliculus* is prepared by freeze-drying the flesh of the mussel and grinding it into a powder. The product is formulated into capsules with the excipients of alfalfa, cellulose and magnesium stearate.

Example 2

Treatment of Systemic Lupus Erythmatosus with a Combination of DMG and PCE Extract Systemic lupus erythmatosus (SLE) is considered to be the prototypic autoimmune disease. SLE is characterized by various degrees of severity with mild forms resulting in minor skin rash and joint pain and severe forms resulting in glomerulonephritis, immune complex disease, severe lymph node enlargement, and multiple organ failure. SLE is further characterized by the development of auto-antibodies against cytoplasmic and nuclear components. In addition to clinical symptoms, the presence of anti-nuclear antibodies is a hallmark of the disease, and its presence is an important indication in the diagnosis of the disease (Tan, 1989, *Adv. Immunology* 44:93). MRI-lpr mice are an accepted and well documented model for SLE (Cohen and Eisenberg, 1991, *Ann. Rev. Immunol.* 9:203; Kotzin, 1996, *Cell* 85:303). These mice display a homozygous genetic defect in the Fas-TNF receptor related to apoptosis. Fas protein is an important pathway for the induction of apoptosis and the Fas protein is responsible for lymphocyte removal. These mice produce a broad spectrum of auto-antibodies against nuclear and cytoplasmic proteins, and the MRI-lpr mice die from classical lupus-like symptoms.

MRI-lpr mice were used to study the effects of a combination of DMG and PCE on components of the immune system and on the progression of the SLE disease. Forty MRI-lpr mice were divided into four groups of ten mice each: a control group, a PCE treated group, a DMG treated group, and a PCE-DMG treated group. The control group was given standard mouse chow and water. The DMG group was given standard mouse chow and water mixed with 34 mg/L of DMG (AANGAMIK® DMG, FoodScience Corporation, Essex Junction, Vt.). The PCE group was given a PCE-mouse chow mix and water. The PCE-DMG combination group was given a PCE-mouse chow mix and DMG water. The PCE supplement used in the studies was a product containing freeze-dried, ground whole *Perna canaliculus* mussel (Perna, FoodScience Corporation, Essex Junction, Vt.). The mice were given food and water ad libitum. It is estimated that the mice, with a size range of 30–50 grams, consumed about 1–3 mg/day of DMG and 2–6 mg/day of PCE. The mice were weighed weekly and 100 ul of blood was collected via orbital bleed on a weekly basis. The collected blood was centrifuged and the serum was recovered and stored at −20° C. for analysis at the end of the twelve week experiment. After twelve weeks, the mice were sacrificed and the spleens, kidneys, and livers were harvested. When the mice were sacrificed, blood was also collected via a cardiac stick. The serum was collected and stored as described above. The spleens were processed and the cells recovered were quantified by flow cytometry using fluorescent anti-CD4, anti-CD8 and anti-CD19 antibodies (Pharmingen, San Diego, Calif.). Cytokine levels in the serum and anti-single stranded and double stranded DNA antibody levels in the serum were determined using an enzyme linked immunosorbent assay (ELISA).

Figure 1:
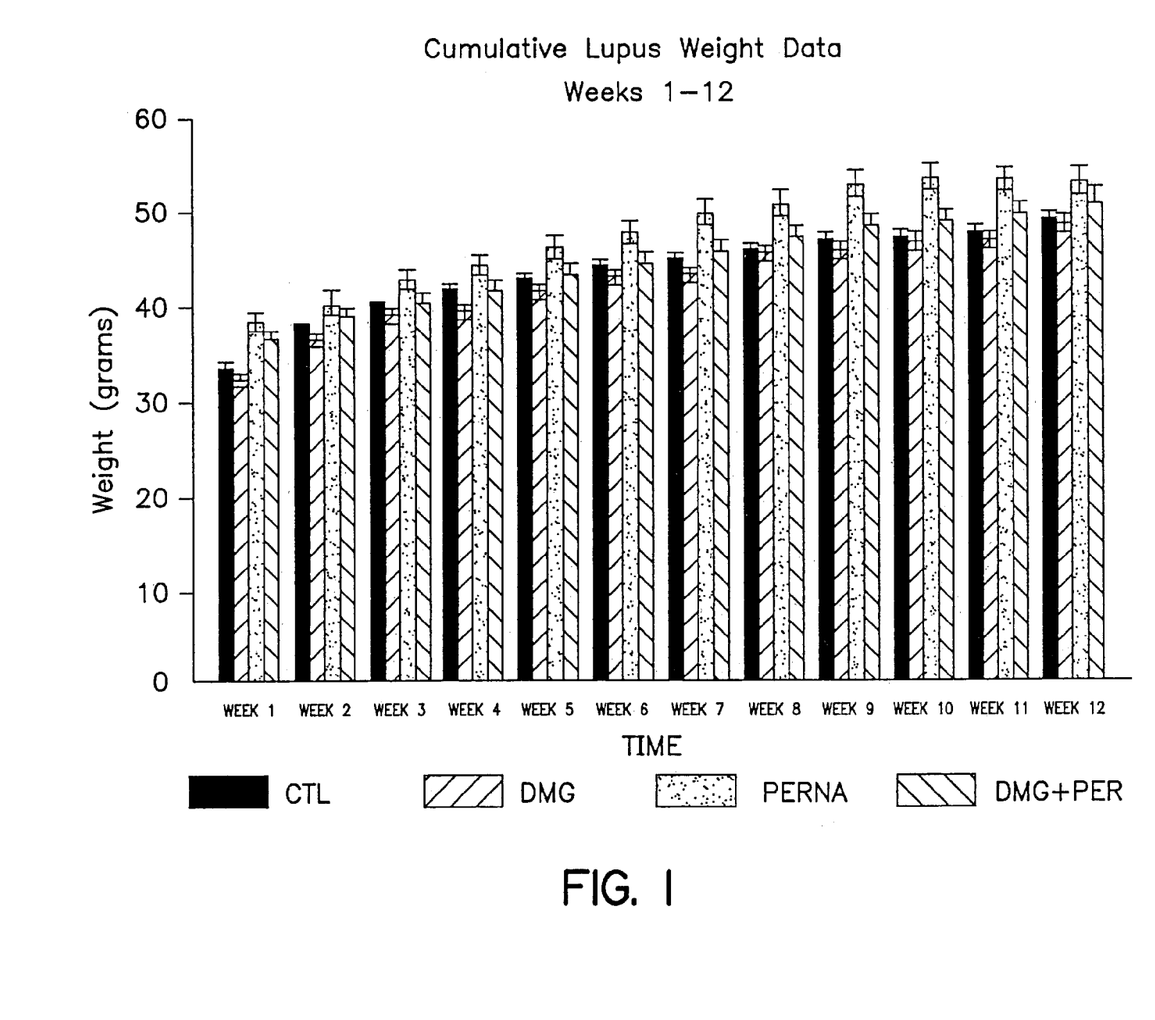
FIG. 1 is a graph showing the weight gain comparisons for control mice, and for mice treated with DMG, PCE, or a combination of DMG and PCE.
Figure 3:
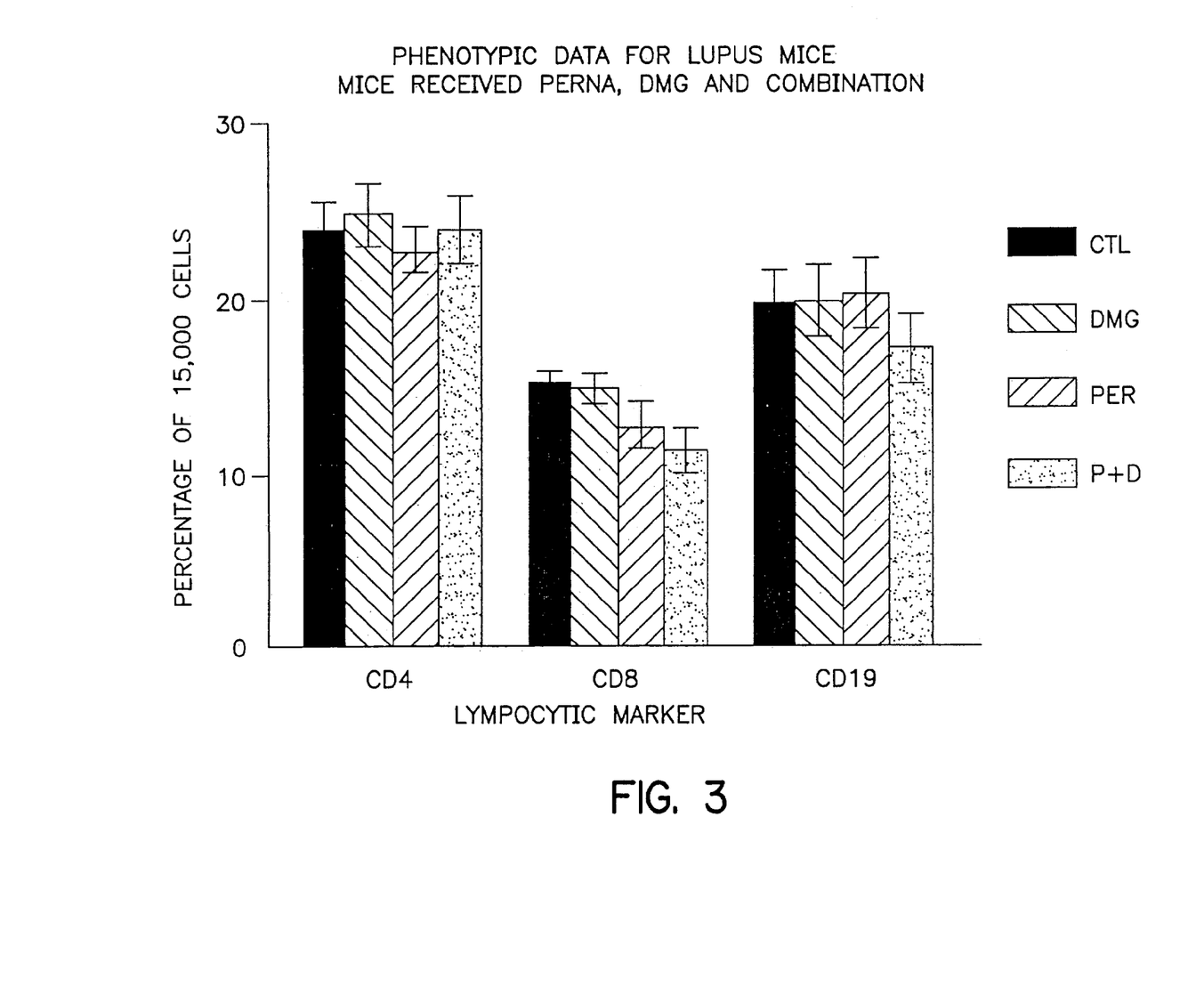
FIG. 3 is a graph comparing lymphocyte population levels, including lymphocytes having CD4, CD8, and CD19 markers, in control mice and in mice treated with DMG, PCE, or a combination of DMG and PCE.

Animals whose diets were supplemented with PCE alone or the DMG-PCE combination experienced a higher weight gain than control or DMG treated animals, indicating that the mice treated with the combination were not adversely affected by the treatment (FIG. 1). A significant decrease in $CD8^+$ T cells was noted with animals fed the standard DMG-PCE combination, with a trend toward lower levels in animals fed only PCE (FIG. 3). A trend toward lower $CD19^+$ B cell percentages was also observed with DMG-PCE treated animals, while animals treated with PCE alone had $CD19^+$ B cell levels comparable to those of controls. No effect of DMG alone on $CD8^+$ T-cell or $CD19^+$ B-cell levels could be detected (FIG. 3).

Figure 2:
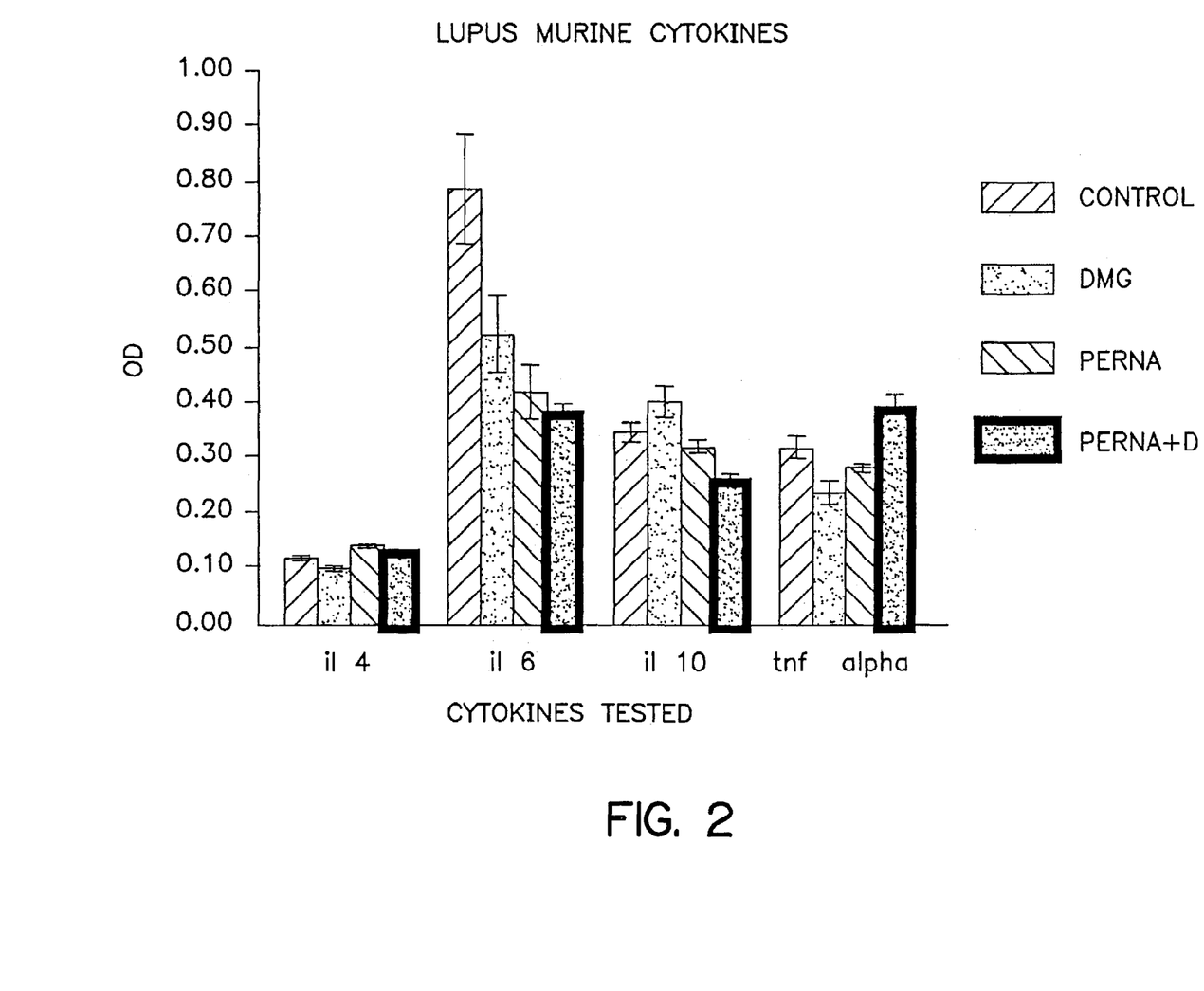
FIG. 2 is a graph comparing cytokine concentrations, including il-4, il-6, il-10, and TNF-α, in control mice and in mice treated with DMG, PCE, or a combination of DMG and PCE.

The effects on cytokine production in mice treated with the DMG-PCE combination was also examined. As shown in FIG. 2, animals treated with the DMG-PCE combination showed significantly lower levels of serum il-6 than either control animals or animals treated with DMG alone. Although animals treated with either DMG or PCE alone had significantly lower levels of il-6 than control animals, animals treated with a combination of the two had even lower levels. DMG-PCE treated animals also showed significantly lower levels of serum il-10 than either control animals or animals treated with either DMG or PCE alone. These changes in cytokine serum levels are indicative of a shift from a Th2 response to a Th1 response. The significant rise in serum levels of tumor necrosis factor (TNF) in DMG-PCE treated animals is also indicative of this shift from a Th2 response to a Th1 response.

Treatment of animals with DMG alone resulted in higher levels of IL-10 than in controls, indicating a shift toward a Th2 response. Although DMG is a known enhancer of antibody production, it is not known whether the enhanced antibody production observed represents pathological IgG2a production. Levels of serum il-10 and TNF-α were comparable in control animals and in animals treated with PCE alone. Therefore, DMG-PCE treatment appeared to shift the lymphocyte response from a Th2 response to a Th1 response, with a concomitant decrease in excess antibody production, including anti-nuclear antibody production as discussed below.

Figure 4:
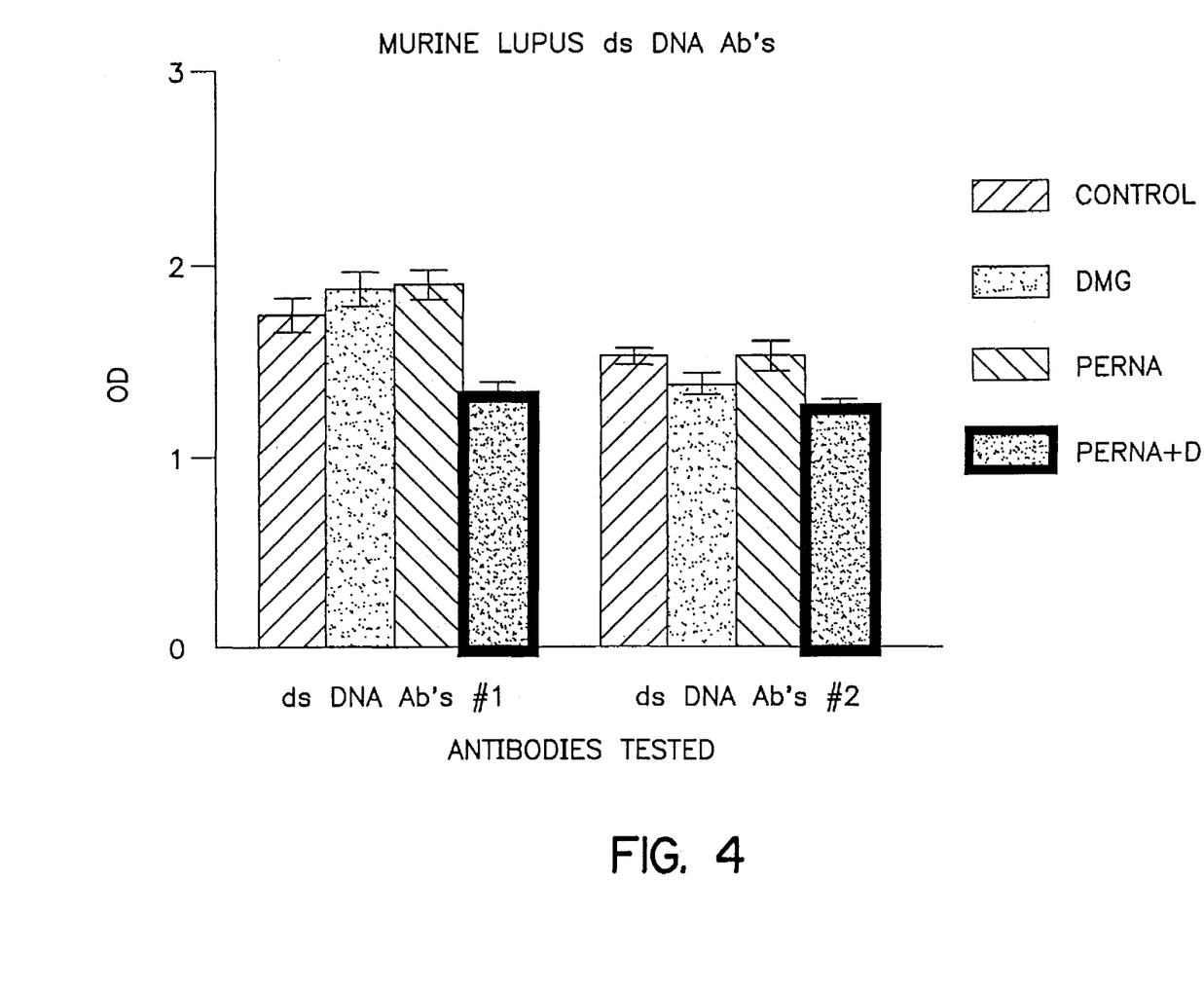
FIG. 4 is a graph comparing concentrations of anti-double stranded DNA antibodies in control mice and in mice treated with DMG, PCE, or a combination of DMG and PCE. Two experiments, (#1) and (#2), were conducted.
Figure 5:
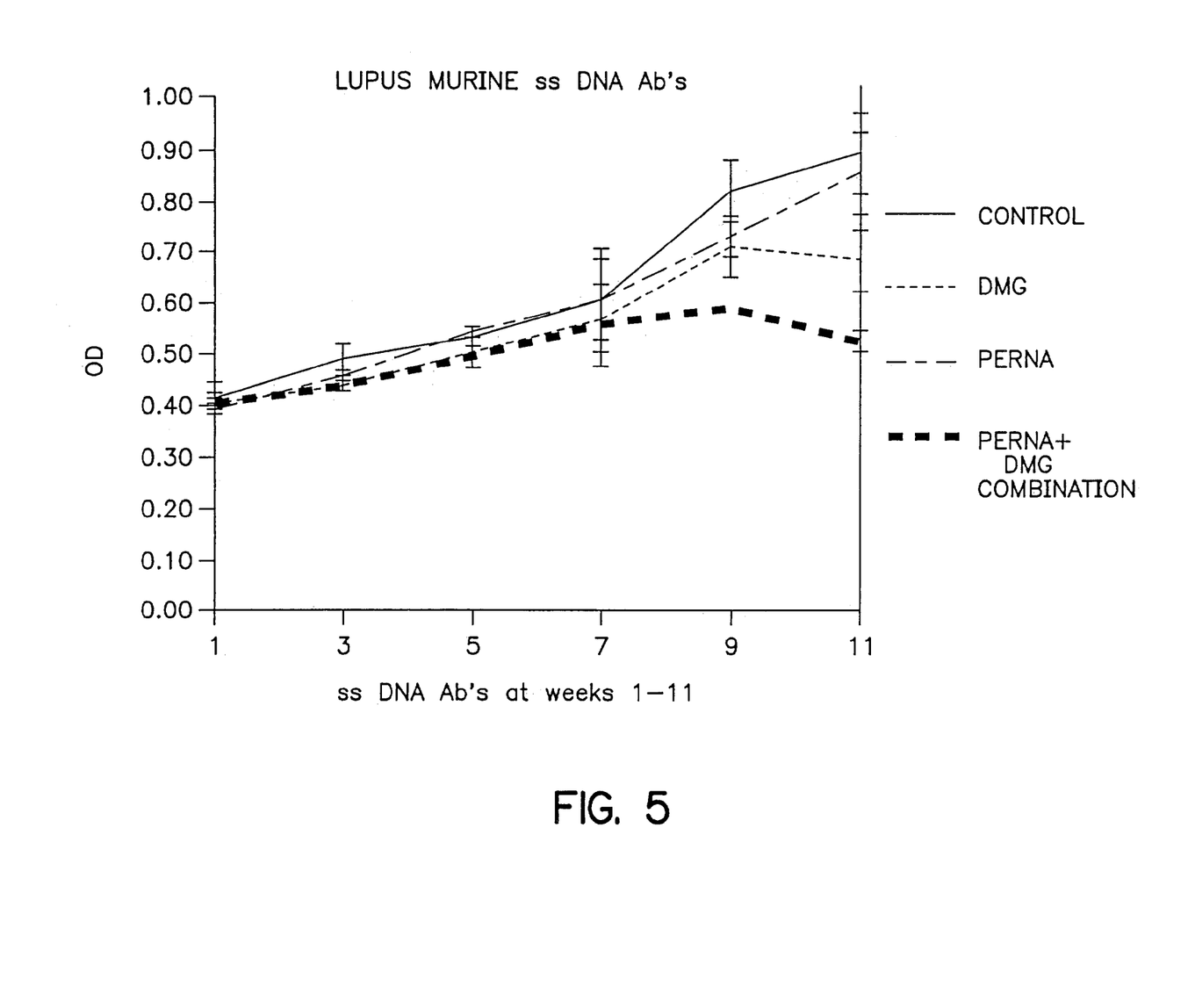
FIG. 5 is a graph comparing concentrations of an anti-single stranded DNA antibodies in control mice and in mice treated with DMG, PCE, or a combination of DMG and PCE.

Levels of anti-nuclear antibodies were also examined in control and treated mice. After eleven weeks of treatment, anti-dsDNA antibody levels in the serum of DMG-PCE treated animals were significantly lower than in control animals or in animals treated with DMG alone or PCE alone (FIG. 4). Even more significantly, anti-ssDNA antibody levels in the serum of DMG-PCE treated animals were in tandem with levels in control animals until the 7th week, when these serum concentrations were found to be lower (FIG. 5). This significant difference was observed to continue until animals were euthanized after the 11th week. Serum levels of anti-ssDNA antibodies in control animals and in animals treated with PCE alone continued to increase throughout the course of treatment. By the 11th week, serum levels in animals treated with DMG alone appeared to be leveling out.

Example 3

Figure 6:
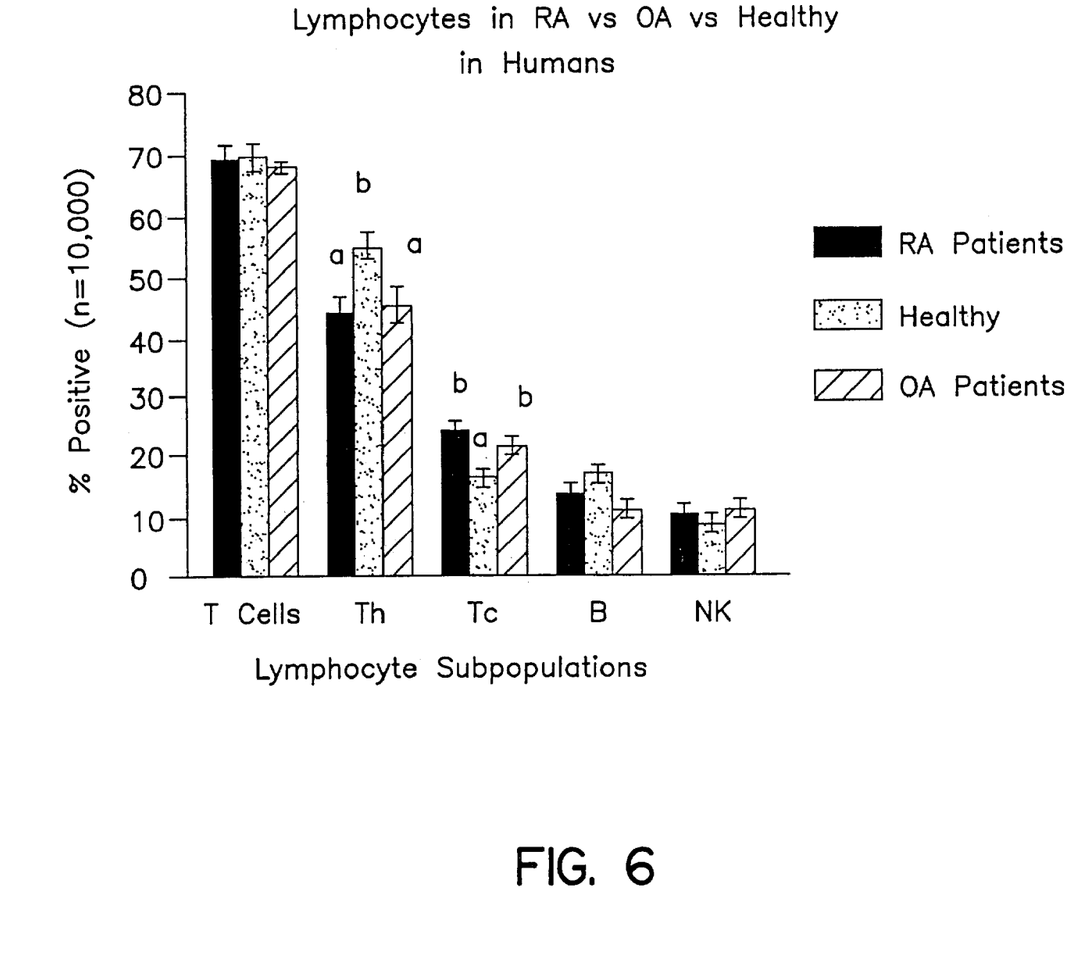
FIG. 6 is a graph comparing lymphocyte populations in healthy human subjects with lymphocyte populations in human subjects with osteoarthritis or rheumatoid arthritis. Cell populations that were measured include total T cells (T Cells), helper T cells (Th) ($CD4^+$), cytotoxic T cells (Tc) ($CD8^+$), B cells (B) ($CD19^+$), and natural killer cells (NK). Within a subpopulation, columns with different superscripts (i.e. a and b) are significantly different ($p \leq 0.01$).

Comparison of Lymphocyte Populations in Healthy Human Subjects with Lymphocyte Populations in Human Subjects with Osteoarthritis or Rheumatoid Arthritis Lymphocyte populations were measured and compared in healthy human subjects versus human subjects with osteoarthritis or rheumatoid arthritis (FIG. 6). Lymphocyte populations measured included total T cells (T Cells), helper T cells (Th) ($CD4^+$ cells), cytotoxic T cells (Tc) ($CD8^+$ cells), B cells (B), and natural killer cells NK). The cell populations were identified by external staining of whole blood lymphocytes using the following antibodies: anti-CD3 antibodies for total T cells; anti-CD4 antibodies for helper T-cells; anti-CD8 antibodies for cytotoxic T; anti-CD5 and anti-CD19 antibodies for B cells; anti-CD56 antibodies for natural killer cells; and anti-CD45 antibodies for monocytes. The antibodies were obtained from either Caltag Corp. or Coulter Corp. and were tagged for analysis on an EPICs 751 flow cytometer (Coulter F1) with a Cicero acquisition module and cyclops analysis software (Cytomation, CA). As shown by the data in FIG. 6, a $CD4^+/CD8^+$ T cell switch was observed in both diseases when compared to healthy controls, with a significant decrease in $CD4^+$ cells in subjects with either disease and a significant increase in $CD8^+$ cells in subjects with either disease.

Example 4

Figure 7:
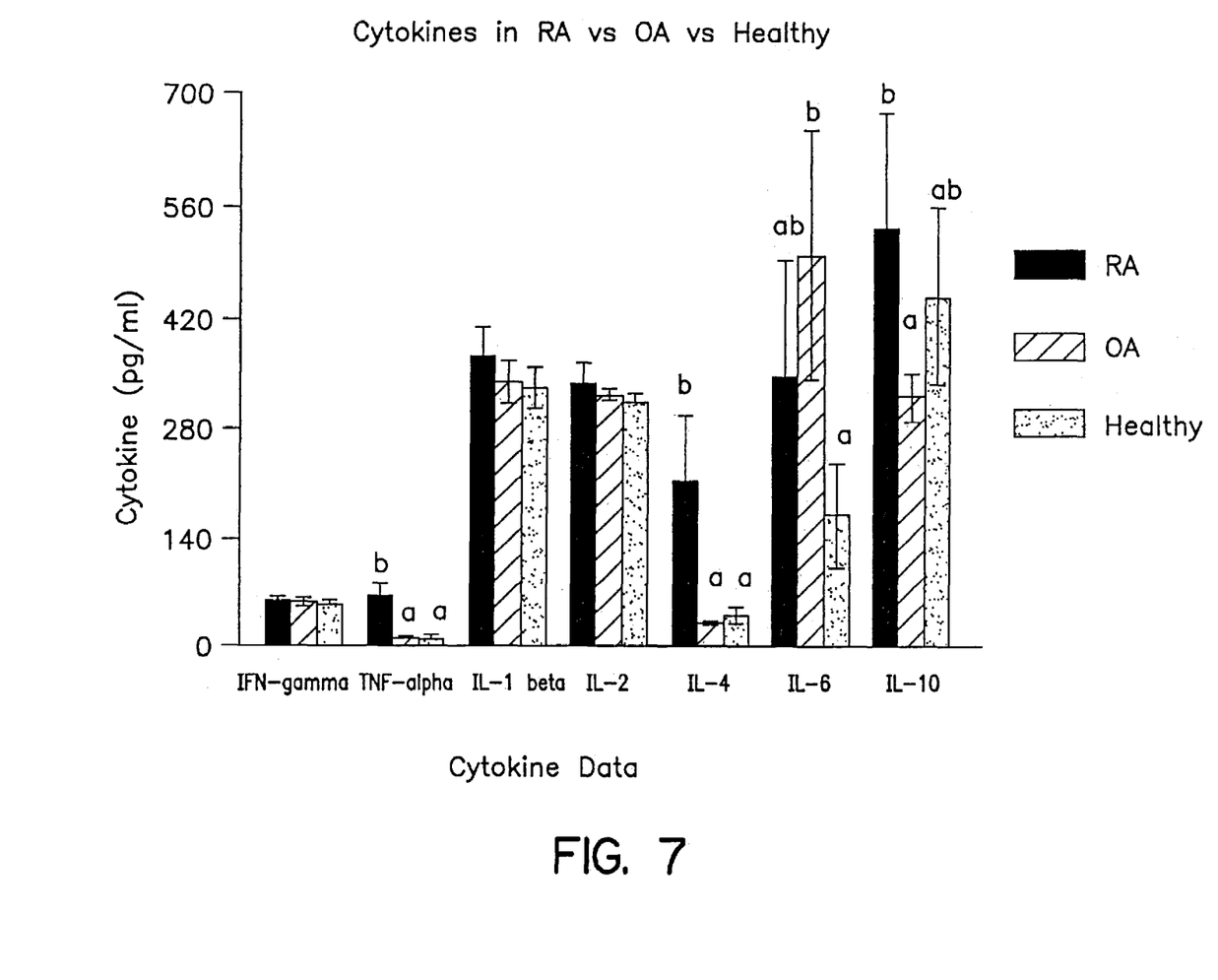
FIG. 7 is a graph comparing cytokine concentrations in healthy human subjects with cytokine concentrations in human subjects with osteoarthritis or rheumatoid arthritis. Within a subpopulation, columns with different superscripts (i.e. a and b) are significantly different (p<0.01).

Comparison of Cytokine Concentrations in Healthy Human Subjects with Cytokine Concentrations in Human Subjects with Osteoarthritis or Rheumatoid Arthritis Cytokine levels were measured and compared in healthy human subjects versus human subjects with osteoarthritis or rheumatoid arthritis (FIG. 7). Cytokines measured included gamma interferon, interleukin 1-beta, interleukin 2, interleukin 4, interleukin 6, interleukin 10 and TNF-α. Cytokines were measured using specific ELISA kits according to the manufacturers instructions (Immunotech, France). Interleukin 6 levels were significantly higher in subjects with either disease than for control subjects. TNF-α levels were significantly increased in subjects with rheumatoid arthritis compared to normal controls, but were not increased in patients with osteoarthritis.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patent applications, patents, and publications cited herein are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for treating lupus erythmatosus, which comprises administering to a patient in need of such treatment an effective amount of N,N-dimethylglycine and a PCE component which comprises freeze-dried and ground whole flesh and organs of the *Perna canaliculus* mussel, wherein the amount of N,N-dimethylglycine administered is from 1 to 500 mg/kg/day and the amount of the PCE component administered is from 1 to 500 mg/kg/day, and wherein the N,N-dimethylglycine and the PCE component are administered separately, or together as a composition, and wherein the N,N-dimethylglycine and the PCE component are each administered orally, or by intramuscular or intraperitoneal injection.

2. The method of claim 1, wherein the PCE component is administered orally.

3. The method of claim 1, wherein the amount of N,N-dimethylglycine administered is from 10 to 100 mg/kg/day and the amount of the PCE component administered is from 10 to 100 mg/kg/day.

4. The method of claim 1, wherein the N,N-dimethylglycine and the PCE component are administered together as a composition.

5. The method of claim 4, wherein the composition is administered orally.

6. The method of claim 4, wherein the amount of N,N-dimethylglycine administered is from 10 to 100 mg/kg/day and the amount of the PCE component administered is from 10 to 100 mg/kg/day.

7. The method of claim 1, wherein the N,N-dimethylglycine and the PCE component are administered separately.

8. The method of claim 7, wherein the N,N-dimethylglycine and the PCE component are both administered orally.

9. The method of claim 7, wherein the amount of N,N-dimethylglycine administered is from 10 to 100 mg/kg/day and the amount of the PCE component administered is from 10 to 100 mg/kg/day.

* * * * *